(12) United States Patent
Monahan et al.

(10) Patent No.: US 7,498,017 B2
(45) Date of Patent: *Mar. 3, 2009

(54) COMPOSITIONS FOR DELIVERING NUCLEIC ACIDS TO CELLS

(75) Inventors: Sean D. Monahan, Madison, WI (US); Vladimir Trubetskoy, Madison, WI (US)

(73) Assignee: Roche Madison Inc., Madison, WI (US)

( * ) Notice: Subject to any disclaimer, the term of this patent is extended or adjusted under 35 U.S.C. 154(b) by 148 days.

This patent is subject to a terminal disclaimer.

(21) Appl. No.: 11/154,494

(22) Filed: Jun. 16, 2005

(65) Prior Publication Data

US 2006/0039860 A1 Feb. 23, 2006

Related U.S. Application Data

(62) Division of application No. 10/445,696, filed on May 27, 2003, now Pat. No. 7,220,400.

(60) Provisional application No. 60/383,201, filed on May 24, 2002, provisional application No. 60/411,332, filed on Sep. 17, 2002.

(51) Int. Cl.
*A61K 51/00* (2006.01)
*A61M 36/14* (2006.01)

(52) U.S. Cl. ............. 424/1.73; 424/1.11; 424/1.65; 548/300.1; 536/22.1

(58) Field of Classification Search ............. 424/1.11, 424/1.37, 1.49, 1.65, 1.69, 1.73, 1.17, 9.1; 548/300.1
See application file for complete search history.

(56) References Cited

U.S. PATENT DOCUMENTS

| | | | |
|---|---|---|---|
| 6,383,811 B2 * | 5/2002 | Wolff et al. | 435/450 |
| 6,818,626 B1 * | 11/2004 | Wolff et al. | 514/44 |
| 6,881,576 B2 * | 4/2005 | Wolff et al. | 435/458 |
| 6,919,091 B2 * | 7/2005 | Trubetskoy et al. | 424/450 |
| 7,033,607 B2 * | 4/2006 | Trubetskoy et al. | 424/450 |
| 7,045,356 B2 * | 5/2006 | Trubetskoy et al. | 435/458 |
| 7,094,605 B2 * | 8/2006 | Wakefield et al. | 435/458 |
| 7,098,030 B2 * | 8/2006 | Rozema et al. | 435/450 |
| 7,098,032 B2 * | 8/2006 | Trubetskoy et al. | 435/458 |
| 7,220,400 B2 * | 5/2007 | Monahan et al. | 424/1.73 |

OTHER PUBLICATIONS

Denny, William A. "DNA Minor Grove Alkylating Agents" Current Medicinal Chemistry 2001, vol. 8, p. 533-544.
Clark, George R. et al. "Structure of a bis-amidinium derivative of Hoescht 33258 complexes to dodecanucleotide d (CGCGAATCGCG)2: the role of hydrogen bonding in minor groove-DNA recognition" Nucleic Acids Research 1997, vol. 25, No. 8, p. 1517-1522.
Thomas, Mini et al. "ENhancing polyethylenimine's delivery of plasmid DNA into mammalian cells" Proceeding from the National Academy of Sciences USA 2002, vol. 99, No. 23, p. 14640-14645.

* cited by examiner

*Primary Examiner*—D. L Jones
(74) *Attorney, Agent, or Firm*—Kirk Ekena; Mark K. Johnson

(57) ABSTRACT

Cyclic amidinium containing compounds and their methods of preparation are described. Compositions containing these compounds facilitate delivery of biologically active polymers to cells in vitro and in vivo.

14 Claims, 4 Drawing Sheets

COMPOSITIONS FOR DELIVERING NUCLEIC ACIDS TO CELLS

CROSS-REFERENCE TO RELATED APPLICATIONS

This application is a divisional of application Ser. No. 10/445,696, filed May 27, 2003, issued as U.S. Pat. No. 7,220,400, which claims the benefit of U.S. Provisional Application No. 60/383,201 filed May 24, 2002 and No. 60/411,332 filed Sep. 17, 2002.

BACKGROUND OF THE INVENTION

Biologically active polymers such as proteins, enzymes, and nucleic acids (DNA and RNA) have been delivered to the cells using amphipathic compounds that contain both hydrophobic and hydrophilic domains. Typically these amphipathic compounds are organized into vesicular structures such as liposomes, micellar, or inverse micellar structures. Liposomes can contain an aqueous volume that is entirely enclosed by a membrane composed of lipid molecules (usually phospholipids) (New 1990). Positively-charged, neutral, and negatively-charged liposomes have been used to deliver nucleic acids to cells. For example, plasmid DNA expression in the liver has been achieved via liposomes delivered by tail vein or intraportal routes. Positively-charged micelles have also been used to package nucleic acids into complexes for the delivery of the nucleic acid to cells Polymers have also been widely used for the delivery of biologically active polymers to cells. A number of drug delivery applications utilize polymer matrices as the drug carrier. Polymers have been used for the delivery of nucleic acids (polynucleotides, oligonucleotides, and RNA's) to cells for research and therapeutic purposes. This application has been termed transfection and gene therapy or anti-sense therapy, respectively. One of the several methods of nucleic acid delivery to the cells is the use of DNA-polycation complexes. It was shown that cationic proteins like histones and protamines or synthetic polymers like polylysine, polyarginine, polyornithine, DEAE dextran, polybrene, and polyethylenimine are effective intracellular delivery agents. Polycations are a very convenient linker for associating specific receptors or ligands with the nucleic acid-polycation complex, and as a result, nucleic acid-polycation complexes can be targeted to specific cell types. Polycations also protect nucleic acid in the complexes against nuclease degradation. This protection is important for both extracellular and intracellular preservation of nucleic acid.

The main mechanism of nucleic acid translocation to the intracellular space might be non-specific adsorptive endocytosis. Gene delivery using cationic polymers may be increased by preventing endosome acidification such as with $NH_4Cl$ or chloroquine. Some polymers, such as polyethylenimine and poly(propyl acrylic) acid, may also possess membrane disruptive or endosomalytic properties. Several reports have attributed the gene delivery properties of polyethylenimine to a buffering or proton sponge effect. Disruption of endosomes has also been reported as a result of linking to the polycation endosomal-disruptive agents such as fusion peptides or adenoviruses.

Polycations can also facilitate nucleic acid condensation. The volume which one DNA molecule occupies in a complex with polycations is dramatically lower than the volume of a free DNA molecule. The size of a DNA/polymer complex is probably critical for gene delivery in vivo. In terms of intravenous injection, DNA needs to cross the endothelial barrier and reach the parenchymal cells of interest. The largest endothelia fenestrae (holes in the endothelial barrier) occur in the liver and have an average diameter of 100 nm. The transepithelial pores in other organs are much smaller, for example, muscle endothelium can be described as a structure which has a large number of small pores with a radius of 4 nm, and a very low number of large pores with a radius of 20-30 nm. The size of the DNA complexes is also important for the cellular uptake process. After binding to the cells the DNA-polycation complex are likely taken up by endocytosis. Therefore, DNA complexes smaller than 100 nm are preferred.

SUMMARY OF THE INVENTION

In a preferred embodiment, we describe compositions for delivering a biologically active polymer to a cell comprising: cyclic amidinium-containing compounds. Cyclic amidiniums are groups derived from the intramolecular cyclization of an amine with an amide (resulting in a dehydrating ring formation) on the same polymer. The resulting ring structure has a formal positive charge, but may occur in a polymer that has on overall positive, negative, or neutral charge. The ring size may be 5 to 9 atoms but most favorably a 5, 6 or 8-membered ring, such as an imidazolinium, a 1,3-piperazinium ring, 1,3-nitrogen-8-membered heterocyclic ring. The amide may be alkyl, aryl, or may have any substitution or functionality. The polymers and compositions of the invention, are useful for the delivery of compounds to cells in vitro and in vivo. Compounds that may be delivered to cells may be selected from the list comprising: polynucleotides, oligonucleotides, DNA, RNA, siRNA, DNA and RNA analogs, and biologically active polymers.

The current invention also relates to compositions comprising: polycations derived from the intramolecular cyclization of acylated linear or branched polyethylenimine. The polymers obtained are copolymers of the subunits selected from the group consisting of: ethyl amine, 2-substituted imidazolinium, and N-acyl-ethyleneamine. A preferred polyimidazolinium is derived from N-propionyl linear polyethylenimine. The polymers and compositions of the invention can be used for the delivery of compounds to cells in vitro and in vivo. Compounds that can be delivered to cells using the described polymers may be selected from the list comprising: polynucleotides, oligonucleotides, DNA, RNA, siRNA, DNA and RNA analogs, biologically active polymers.

The present invention provides for the transfer of polynucleotides, and other biologically active polymers into cells in vitro and in vivo, comprising: associating the biologically active polymer with a compound selected from the group consisting of: cyclic amidinium-containing compounds, poly cyclic amidinium-containing compounds, imidazolinium-containing compounds, polyimidazolinium compounds, imidazoline-containing compounds, polyimidazoline compounds, 1,3-piperazinium ring-containing compounds and poly-1,3-piperazinium ring compounds; and delivering the complex to the cell. The complex may be delivered intravascularly, intrarterially, intravenously, orally, intraduodenaly, via the jejunum (or ileum or colon), rectally, transdermally, subcutaneously, intramuscularly, intraperitoneally, intraparenterally, via direct injections into tissue, via mucosal membranes, or into ducts of the salivary or other exocrine glands. The polymer may be modified to contain one or more functional groups that enhance delivery of the polynucleotide of other biologically active polymer to the cell.

Further objects, features, and advantages of the invention will be apparent from the following detailed description when taken in conjunction with the accompanying drawings.

DETAILED DESCRIPTION OF THE INVENTION

Figure 1:
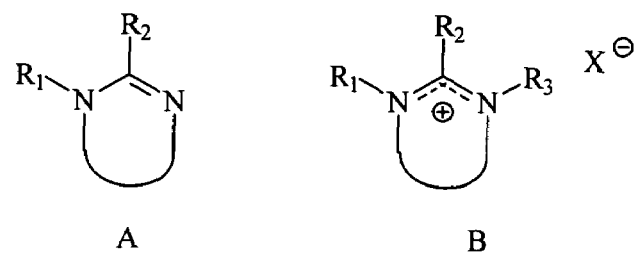
FIG. 1A-1B. Illustrations of the chemical structures for (A) cyclic amidine and (B) cyclic amidinium.

We describe a new class of cyclic amidinium-containing compounds (FIG. 1) that facilitate delivery of biologically active polymers to cells. Specifically, the invention relates compounds containing cationic heterocyclic ring structures derived from the intramolecular 1,2-addition of an amine to an amide, followed by a dehydration. Polymers with an amine four to eleven, and more preferably four to seven, bonds away from an amide carbonyl which is able to undergo this intermolecular cyclization are envisioned in this invention. These polymers contain 1,3-heterocyclic ring systems that possess a formal positive charge. The amide can be formed on a preformed polymer via an acylation reaction, well know in the art. Additionally, an amide containing polymer may be synthesized; for example, the polymer resulting from the polymerization of a 2-oxazoline. A controlled amide hydrolysis can be conducted to synthesize a polymer with the desired proportion of amide containing units and free amine (or protonated amine salt) containing units. The resulting polymer can then be buffered between pH 2-8 and left to undergo the cyclization reaction. These polymers may be selected from the list comprising: partially acylated polyethyleinimines (lPEI, brPEI), partially acylated polyvinylamine, partially acylated polyallylamine, and partially acylated polypropylamine. The ring structures formed may be selected from the list comprising: imidazolinium rings, 1,3-piperazinium rings, and 1,3-nitrogen-8-membered heterocyclic ring.

FIG. 1A depicts an amidine ring. The amidine ring may be alkylated on the nitrogen to afford an amidinium ring (FIG. 1B). The amidinium ring can also form from the intramolecular cyclization and dehydration of an amide and an amine.

In an amidinium (amidinium subunit), substituents R1, R2, R3 can independently be a hydrogen radical or a carbon radical with any substitution. The ring can be from 5 to 12 atoms, and can contain additional heteroatoms in addition to the 1,3-Nitrogen atoms. Additionally, the ring can be substituted in other positions, independently being a hydrogen radical, a carbon radical with any substitution, or a heteroatom radical with any substitution. The counterion (X) can be any counterion. Counterions include, but are not limited to chloride, bromide, iodide, and tosylate.

A polyamidinium is a polymer (random copolymer, block copolymer, or other copolymer) containing two or more amidinium subunits. A polyamidinium also means a homopolymer of the amidinium subunit. The amidinium subunit can be in the main chain of the polymer or as a side chain off of the polymer main chain. The polymer can be a net neutral polymer, a polycation, or a polyanion.

A poly-2-amidine is a polymer (random polymer, or block polymer) containing one or more amidine subunits. A poly-2-amidine also means a homopolymer of the 2-amidine subunit. The amidine subunit can be in the main chain of the polymer or as a side chain off of the polymer main chain. The polymer can be a net neutral polymer, a polycation, or a polyanion.

In a 2-amidine (amidine subunit), substituents R1, R2 can independently be a hydrogen radical or a carbon radical with any substitution. The ring can be from 5 to 12 atoms, and can contain additional heteroatoms in addition to the 1,3-Nitrogen atoms. Additionally, the ring can be substituted in other positions, independently being a hydrogen radical, a carbon radical with any substitution, or a heteroatom radical with any substitution.

Figure 2:
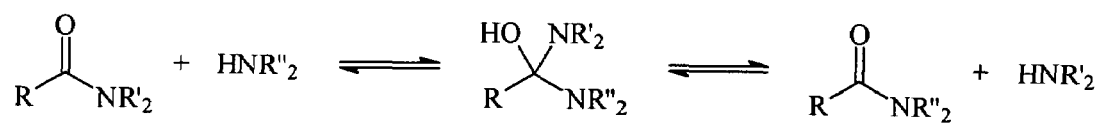
FIG. 2. Illustration of a transamidation reaction.

Amides undergo a variety of chemical transformations. For example, amines are known to react with amides or lactams (cyclic amides) in a transamidation reaction, resulting in the formation of a new amide bond (and a corresponding ring expansion product in the case of lactams) (Chimishkyan 1985; Garcia 1982; Stach 1988; Krammer 1977; Krammer 1978; Askitoglu 1985). Transamidation reactions are know to be substitution dependent on both the amine and the amide. FIG. 2

Figure 3:
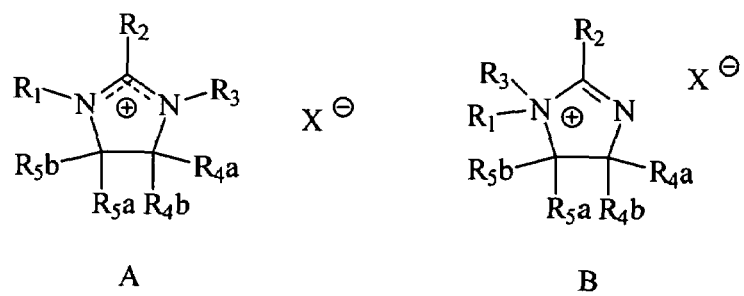
FIG. 3. Illustrations of the chemical structures for imidazolinium heterocyclic rings.
Figure 4:
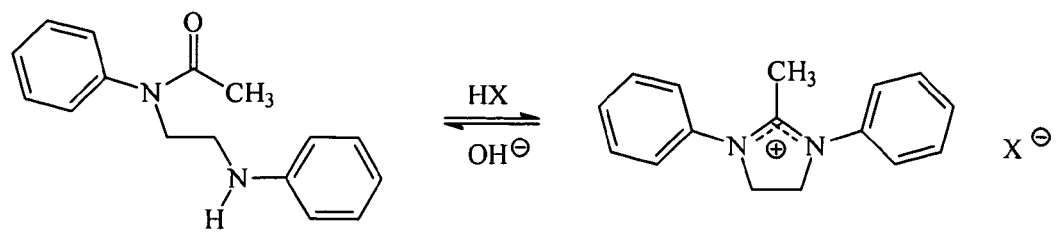
FIG. 4. Illustration of imidazolinium formation from N-acyl-N,N'-diphenyl-ethylenediamine FIG. 5. Illustration of imidazolinium formation from the N-alkylation of an imidazoline ring.

Intramolecular transamidation reactions on both alkyl amides and aryl amides have been reported. Intramolecular reactions between amines and amides have also been reported. In a number of studies, a dehydration of the initial addition product has been observed. This reaction leads to the formation of a heterocyclic ring, in particular the formation of an imidazolinium ring system (FIG. 3A). (May et al. 1951; Jaenicke et al 1959; Hafferl, et al. 1963; Barnett et al. 1966). In particular, the cyclization reaction has been studied on monoacylated derivatives of N,N'-diphenylethylenediamine (FIG. 4). As the imidazolinium ring (FIG. 4) is formed in the cyclization, there is a shift in the UV absorbance for the material, with a new absorbance growing in at λ=220-240 nm range. Reports indicate that the reaction is reversible, depending on the pH of the solution, favoring an imidazolinium under near neutral to acidic conditions, and as a ring opened β-amino amide under basic conditions. In addition to the additiondehydration preparation methods, an imidazolinium ring can be formed via the N-alkylation of the corresponding imidazoline (FIG. 5) (Anderson et al. 1986; Gruseck et al. 1987; Fernandez et al. 1987; Salerno et al. 1992; Perillo et al. 1975), through a nitrilium ion cyclization (Leonard 1965; Pfeil et al. 1965; Leonard et al. 1967), or via a cyclization reaction of a diazapentadinium salt (Lloyd et al. 1978).

Figure 6:
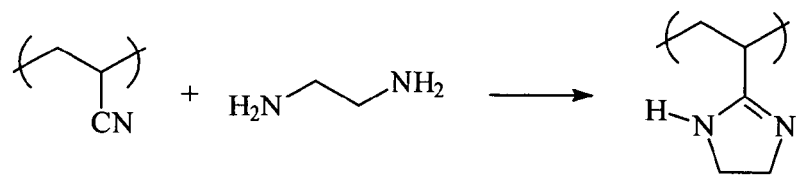
FIG. 6. Illustration of the formations of a polyimidazoline polymer and a poly-imidazolinium polymer.
Figure 6:
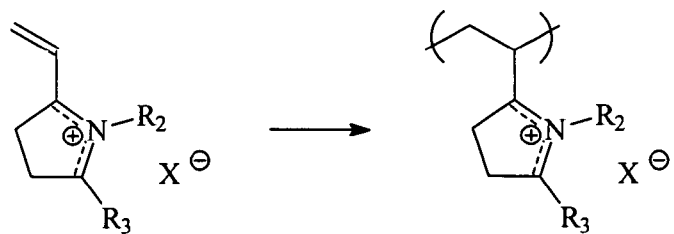

Imidazolinium systems have been developed as surfactants for use as corrosion inhibitors. Additionally, imidazolinium lipids have been prepared, and formulated with DNA in a complex (Lasic et al. 1997), and with DNA for an in vivo liposomal delivery system (Niven et al. 1998). Imidazoline and imidazolinium polymers have also been prepared (FIG. 6). These polymer systems have found use as flocculation aids for the dewatering of sludge. We now show that poly cyclic amidinium systems are useful for delivery of nucleic acid to cells.

Figure 7:
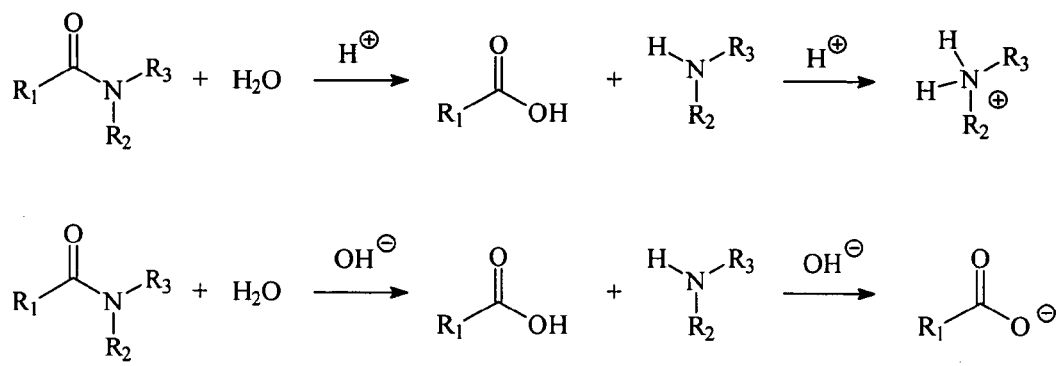
FIG. 7. Illustrations for the acid hydrolysis and base hydrolysis of an amide.

Hydrolysis of amides is a well know method in the art, and can be accomplished under both acid and base catalyzed procedures (FIG. 7). Both methods result in the formation of 1 equivalent of carboxylic acid (or carboxylate ion) and 1 equivalent of amine (or ammonium ion), and are essentially irreversible. Generally, base catalyzed amid hydrolysis is less reliable than acidic hydrolysis, and is therefore not generally used. Amide hydrolysis is not as facile as the hydrolysis of esters, and usually requires more stringent conditions, such as elevated temperature.

Polyimidazolinium: A polyimidazolinium is a polymer (random copolymer, block copolymer, or other copolymer) containing two or more imidazolinium subunits. A polyimidazolium also means a homopolymer of the imidazolinium subunit. The imidazolinium subunit can be in the main chain of the polymer or as a side chain off of the polymer main chain. The polymer can be a net neutral polymer, a polycation, or a polyanion.

Figure 5:
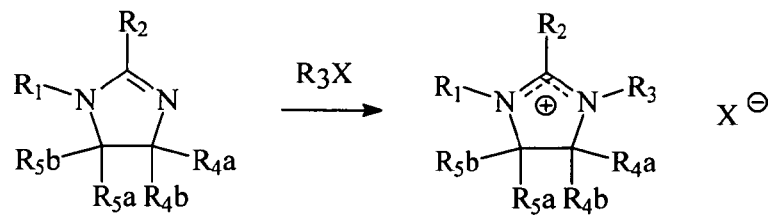

Imidazolinium Subunit: In an imidazolinium (imidazolinium subunit), substituents R1, R2, R3, R4$a$, R4$b$, R5$a$, and R5$b$ (FIG. 3) can independently be a hydrogen radical or a carbon radical with any substitution. The counterion (X) can be any counterion. Counterions include, but are not limited to chloride, bromide, iodide, and tosylate. An imidazolinium ring can be formed via the N-alkylation of the corresponding imidazoline (FIG. 5).

Poly-2-Imidazoline: A poly-2-imidazoline is a polymer (random polymer, or block polymer) containing two or more imidazoline subunits. A poly-2-imidazoline also means a homopolymer of the 2-imidazoline subunit. The imidazoline subunit can be in the main chain of the polymer or as a side chain off of the polymer main chain. The polymer can be a net neutral polymer, a polycation, or a polyanion.

Figure 8:
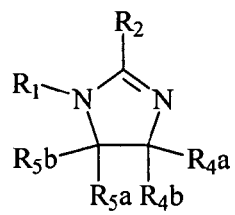
FIG. 8. Illustration of the chemical structure for 2-imidazoline.

2-Imidazoline Subunit: In a 2-imidazoline (imidazoline subunit), substituents R1, R2, R4$a$, R4$b$, R5$a$, and R5$b$ (FIG. 8) can independently be a hydrogen radical or a carbon radical with any substitution.

Poly-1,3-piperazinium: A poly-1,3-piperazinium is a polymer (random copolymer, block copolymer, or other copolymer) containing two or more 1,3-piperazinium subunits. A poly1,3-piperazinium also means a homopolymer of the 1,3-piperazinium subunit. The 1,3-piperazinium subunit can be in the main chain of the polymer or as a side chain off of the polymer main chain. The polymer can be a net neutral polymer, a polycation, or a polyanion.

Figure 9:
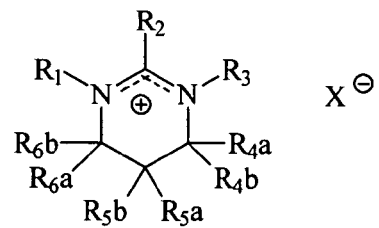
FIG. 9. Illustration of the chemical structure for 1,3-piperazinium.

1,3-Piperazinium (1,3-Piperazinium Subunit): (FIG. 9) In an 1,3-piperazinium (1,3-piperazinium Subunit), substituents R1, R2, R3, R4$a$, R4$b$, R5$a$, R5$b$, R6$a$, and R6$b$ can independently be a hydrogen radical or a carbon radical with any substitution. The counterion (X) can be any counterion. Counterions include, but are not limited to chloride, bromide, iodide, and tosylate.

Figure 10:
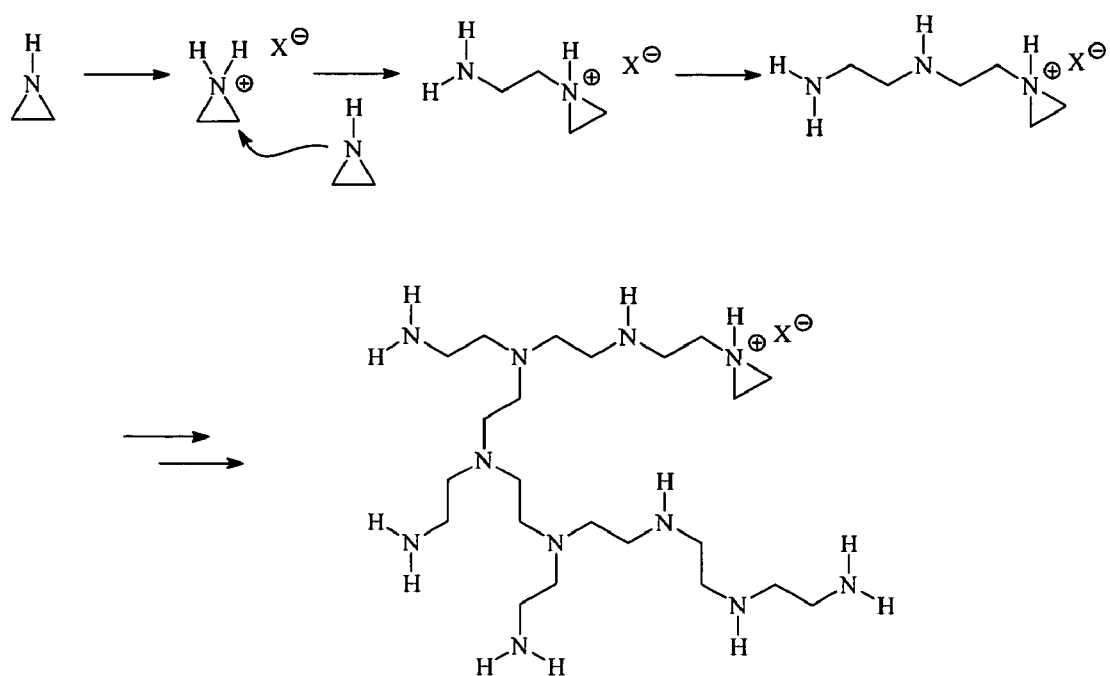
FIG. 10. Illustration of the chemical polymerization to form branched polyethyleneimine.

Poly cyclic amidinium polymers can be prepared from a class of polymers called polyethylenimines. Polyethylenimines themselves have frequently been used in the area of nucleic acid delivery. Polyethylenimine is known in two versions prepared via two distinctive polymerization processes. Branched polyethyleneimine (brPEI) is prepared through the polymerization of aziridine (ethyleneimine) (FIG. 10). During the polymerization reaction, the primary and secondary amines formed can act as nucleophiles, attacking another aziridinium molecule to produce to a highly branched structure. The composition of commercially available brPEI has recently been evaluated to contain an amino group ratio of primary amine:secondary amine:tertiary amine of 1:1:1 (Kissel 2000). BrPEI can also be polymerized under conditions to obtain a lower degree of branching, resulting in an amino group ratio of primary amine:secondary amine:tertiary amine of 1:2:1.

Figure 11:
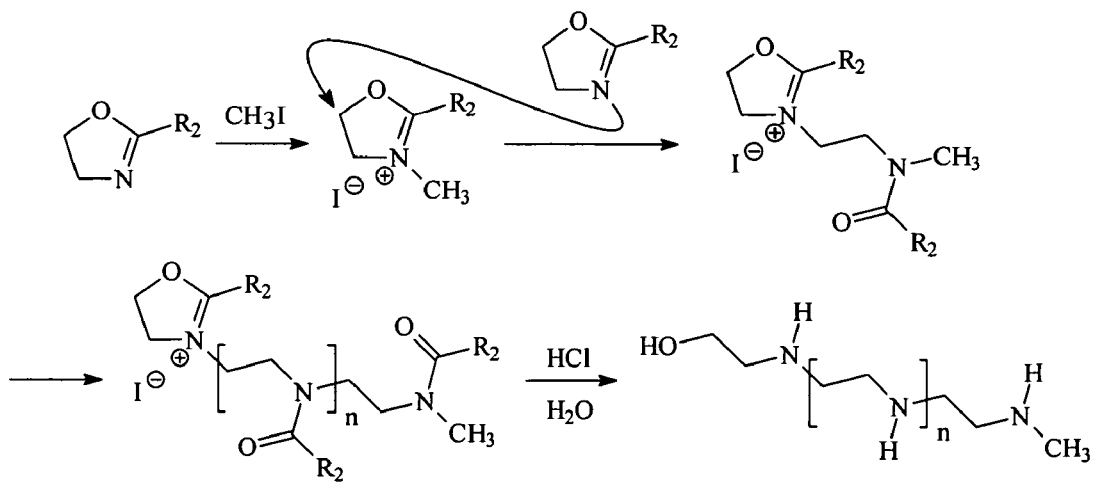
FIG. 11. Illustration of the chemical polymerization to form linear polyethyleneimine.

Linear polyethyleneimine (lPEI) has been shown to exhibit lower cytotoxicity as compared with brPEI, and is an effective gene transfer agent. (Boussif et al. 1995; Behr 1999; Behr 1999; Reny 1998, U.S. Pat. No. 6,013,240; Park et al 2001). Linear PEI is obtained via a ring-opening polymerization of N-alkyl-2-oxazoline, followed by the acid-induced deprotection of the resulting amide (FIG. 11). The polymer is represented by the general formula: HO—$(CH_2)_2$N—$(CH_2$—$CH_2$—NH$)_n$-$(CH2)_2$—N—R, wherein the R group is derived from the initiator used in the polymerization reaction (the figure depicts the final oxazolinium to be hydrolysed to the terminal hydroxyl). For example, if the polymerization is initiated with methyl iodide, the R group in the structure would be $CH_3$. Linear PEI sold for gene therapy applications (Polyplus-transfection SAS, JetPEI; Fermentas; ExGen500), has been described as a linear polymer of ethylamine, containing all secondary amines, as depicted in figure.

Polyethyleneimines can be acylated on the nitrogen atom according to well know methods in the art. The resulting polymers have an amide carbonyl four bonds from an amine. These polymers can be taken up in aqueous solutions at or below pH 8, and gently warmed or stored for periods at RT to facilitate the cyclization reaction to form the cyclic amidinium ring, in particular a imidazolinium ring. The resulting polymer is therefore a combination of ethylenimine, N-acyl ethylenimine (from amides that did not cyclize), and 2-substituted imidazolinium monomers. The proportion of the monomers in the final polymer can be controlled by the level of acylation of the polyethylenimine. Additionally, it is envisioned that additional functionality can be easily included in the system by attaching the functionality to a nitrogen atom on the polyethylenimine via an acylation. The resulting amide would be available to undergo the cyclization reaction, affording a 2-substituted imidazolinium that contains the functionality tethered to the 2 position of the imidazolinium ring.

The size of a nucleic acid/polycation complex may be a factor for gene delivery to cells, particularly in vivo. Often, the size of a nucleic acid of interest is large, too large to facilitate delivery without compacting, or condensing, the nucleic acid. For in vivo delivery, the complex needs to cross the endothelial barrier to reach parenchymal cells. The largest endothelial fenestrae (holes in the endothelial barrier) occur in the liver and have average diameter of 100 nm. The transepithelial pores in other organs are much smaller. Muscle endothelium, for example, can be described as a structure which has a large number of small pores, of radius 4 nm, and a very low number of large pores with a radius of 20-30 nm. The size of the complex may also be important for cellular uptake, with smaller particles being more readily endocytosed.

There are two major approaches for compacting nucleic acid: 1. Multivalent cations with a charge of three or higher have been shown to spontaneously condense nucleic acid under appropriate buffer conditions. These multivalent cations include spermidine, spermine, $Co(NH_3)_6^{3+}$, $Fe^{3+}$, and natural or synthetic polymers such as histone H1, protamine, polylysine, and polyethylenimine. One analysis has shown nucleic acid condensation to be favored when 90% or more of the charges along the sugar-phosphate backbone are neutralized (Wilson et al. 1979). 2. Polymers (neutral or anionic) can increase repulsion between nucleic acid and its surroundings, and have been shown to compact nucleic acid. Most significantly, spontaneous nucleic acid self-assembly and aggregation process have been shown to result from the confinement of large amounts of nucleic acid, due to excluded volume effect (Strzelecka 1990a; Strzelecka 1990b). Since self-assembly is associated with locally or macroscopically crowded nucleic acid solutions, it is expected that nucleic acid insertion into small water cavities with a size comparable to the nucleic acid will tend to form mono or oligomolecular compact structures.

The mechanism of nucleic acid condensation is not clear. The electrostatic force between unperturbed helices arises primarily from a counterion fluctuation mechanism requiring multivalent cations and plays a major role in nucleic acid condensation. The hydration forces predominate over electrostatic forces when the nucleic acid helices approach closer then a few water diameters. In a case of nucleic acid/polymeric polycation interactions, nucleic acid condensation is a more complicated process than the case of low molecular weight polycations. Different polycationic proteins can generate toroid and rod formations with nucleic acid at a positive to negative charge ratio of 2-5. T4 DNA complexes with polyarginine or histone can form two types of structures; an elongated structure with a long axis length of about 350 nm (like free DNA) and dense spherical particles. Both forms exist simultaneously in the same solution. The reason for the co-existence of the two forms can be explained as an uneven distribution of the polycation chains among the nucleic acid molecules. The uneven distribution generates two thermodynamically favorable conformations.

The electrophoretic mobility of nucleic acid/polycation complexes can change from negative to positive in the presence of excess polycation. It is likely that large polycations don't completely align along nucleic acid but form polymer loops that interact with other nucleic acid molecules. The rapid aggregation and strong intermolecular forces between different nucleic acid molecules may prevent the slow adjustment between helices needed to form tightly packed orderly particles.

Poly cyclic amidinium polymers may be prepared such that they have sufficient positive charge to form complexes with nucleic acid. Alternatively, cyclic amidinium monomers and small poly cyclic amidinium monomers may by polymerized using a process termed template polymerization. Low molecular weight cations with valency, i.e. charge, <+3 fail to condense DNA in aqueous solutions under normal conditions. However, cationic molecules with the charge <+3 can be polymerized in the presence of polynucleic acid and the resulting polymers can cause the polynucleic acid to condense into compact structures. Such an approach is known in synthetic polymer chemistry as template polymerization. During this process, monomers (which are initially weakly associated with the template) are positioned along a template's backbone, thereby promoting their polymerization. Weak electrostatic association of the nascent polymer and the template becomes stronger with chain growth of the polymer. Trubetskoy et al used two types of polymerization reactions to achieve DNA condensation: step polymerization and chain polymerization (Trubetskoy et al. 1998; U.S. Pat. No. 08/778, 657; U.S. Pat. No. 09/000,692; U.S. Pat. No. 97/24,089; U.S. Pat. No. 09/070,299; U.S. Pat. No. 09/464,871). Bis( 2-aminoethyl)-1,3-propanediamine (AEPD), a tetramine with 2.5 positive charges per molecule at pH 8 was polymerized in the presence of plasmid DNA using cleavable disulfide amino-reactive cross-linkers dithiobis (succinimidyl propionate) and dimethyl-3,3'-dithiobispropionimidate. Both reactions yielded DNA/polymer complexes with significant retardation in agarose electrophoresis gels, thus demonstrating significant binding and DNA condensation. Blessing et al used a bisthiol derivative of spermine and reaction of thiol-disulfide exchange to promote chain growth. The presence of DNA accelerated the polymerization reaction as measured by the rate of disappearance of free thiols in the reaction mixture (Blessing et al. 1998).

In order to increase the stability of a poly(cyclic amidinium)/nucleic acid complex, the polymer may be crosslinked. The stability of nucleic acid particles, based on polynucleic acid condensation, is generally low in vivo or in the presence of other polyanions because the complexes easily engage in polyanion exchange reactions. The process of exchange consists of two stages: 1) rapid formation of a triple nucleic acid-polycation-polyanion complex, 2) slow substitution of one polyanion (nucleic acid) with another. At equilibrium conditions, this process results in formation of a new binary complex and an excess of a third polyanion. The presence of low molecular weight salt can greatly accelerate such exchange reactions, which often result in complete disassembly of condensed nucleic acid particles. Hence, it is desirable to obtain more colloidally stable structures in which the nucleic acid is retained in condensed form in complex with the polycation independent of environment conditions.

In typical nucleic acid/polycation complexes, in which the nucleic acid is completely condensed, unpaired positive charges on the polycation remain available. If the polycation contains reactive groups, such as primary amines, these unpaired positive charges may be modified. This modification allows practically limitless possibilities of modulating colloidal properties of the complexes via chemical modifications of the complex. We have demonstrated the utility of such reactions using a DNA/poly-L-lysine (DNA/PLL) system crosslinked with the bifunctional cross-linking reagent dimethyl-3,3'-dithiobispropionimidate (DTBP) which reacts with primary amino groups (Trubetskoy et al. 1999b; U.S. Pat. No. 08/778,657; U.S. Pat. No. 09/000,692; U.S. Pat. No. 97/24,089; U.S. Pat. No. 09/070,299; U.S. Pat. No. 09/464, 871). Similar results were achieved with other polycations including poly(allylamine) and histone H1. The use of another bifunctional reagent, glutaraldehyde, has been described for stabilization of DNA complexes with cationic peptide CWK18 (Adam et al. 1999).

The caging approach described above could lead to more colloidally stable condensed nucleic acid-containing particles. However, for some delivery applications it may be desirable to alter the surface charge of a nucleic acid/polycation complex. The phenomenon of surface recharging is well known in colloid chemistry and is described in great detail for lyophobic/lyophilic systems (for example, silver halide hydrosols). Addition of polyion to a suspension of latex particles with oppositely-charged surface leads to the permanent absorption of this polyion on the surface and, upon reaching appropriate stoichiometry, reversing the surface charge. We have demonstrated that similar layering of polyelectrolytes can be achieved on the surface of DNA/polycation particles (Trubetskoy et al. 1999b). The principal DNA-polycation (DNA/pC) complex used in this study was DNA/PLL (1:3 charge ratio) formed in low salt 25 mM HEPES buffer and recharged with increasing amounts of various polyanions. The DNA particles were characterized after addition of a third polyion component to a DNA/polycation complex (Trubetskoy et al. 1999c). It was found that certain polyanions, such as poly(methacrylic acid) and poly(aspartic acid), decondensed DNA in DNA/PLL complexes. Polyanions of lower charge density, such as succinylated PLL and poly (glutamic acid), did not decondense DNA in DNA/PLL (1:3)

complexes even when added in 20-fold charge excess to PLL. Further studies have found that displacement effects are salt-dependent. Measurement of ζ-potential of DNA/PLL particles during titration with SPLL revealed the change of particle surface charge at approximately the charge equivalency point. Thus, it can be concluded that addition of low charge density polyanion to the cationic DNA/PLL particles results in particle surface charge reversal while maintaining condensed DNA core intact. Finally, DNA/polycation complexes can be both recharged and crosslinked or caged (U.S. Pat. No. 08/778,657, U.S. Pat. No. 09/000,692, U.S. Pat. No. 97/24, 089, U.S. Pat. No. 09/070,299, and U.S. Pat. No. 09/464,871). This recharging polyanion layer can be crosslinked to itself or to the polycations in the complex to increase colloidal stability.

Several modifications of nucleic acid/cation particles have been created to circumvent the nonspecific interactions of nucleic acid-cation particles and the toxicity of cationic particles. Examples of these modifications include attachment of steric stabilizers, e.g. polyethylene glycol, which inhibit nonspecific interactions between the cation and biological polyanions.

A polymer is a molecule built up by repetitive bonding together of smaller units called monomers. In this application the term polymer includes both oligomers, which have two to about 80 monomers, and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (Stevens 1990). Template polymerization can be used to form polymers from daughter polymers.

Chain Polymerization: In chain-reaction polymerization growth of the polymer occurs by successive addition of monomer units to limited number of growing chains. The initiation and propagation mechanisms are different and there is usually a chain terminating step. The polymerization rate remains constant until the monomer is depleted. Monomers containing (but not limited to) vinyl, acrylate, methacrylate, acrylamide, methacrylamide groups can undergo chain reaction which can be radical, anionic, or cationic. Chain polymerization can also be accomplished by cycle or ring opening polymerization. Several different types of free radical initiators could be used that include peroxides, hydroxy peroxides, and azo compounds such as 2,2'-Azobis(-amidinopropane) dihydrochloride (AAP).

Types of Monomers

A wide variety of monomers can be used in the polymerization processes. These include positive charged organic monomers such as amine salts, imidine, guanidine, imine, hydroxylamine, hydrozyine, heterocycle (salts) like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Monomers can also be intercalating agents such as acridine, thiazole orange, or ethidium bromide. Monomers can also contain chemical moieties that can be modified before or after the polymerization including (but not limited to) amines (primary, secondary, and tertiary), amides, carboxylic acid, ester, hydroxyl, hydrazine, alkyl halide, aldehyde, and ketone.

A polycation is a polymer containing a net positive charge. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule.

The polymers have other functional groups that increase their utility. These groups can be incorporated into monomers prior to polymer formation or attached to the polymer after its formation.

Functional group. Functional groups include cell targeting signals, nuclear localization signals, compounds that enhance release of contents from endosomes or other intracellular vesicles (releasing signals), and other compounds that alter the behavior or interactions of the compound or complex to which they are attached.

Cell targeting signals are any signals that enhance the association of the biologically active polymer with a cell. These signals can modify a biologically active polymer such as drug or nucleic acid and can direct it to a cell location (such as tissue) or location in a cell (such as the nucleus) either in culture or in a whole organism. The signal may increase binding of the compound to the cell surface and/or its association with an intracellular compartment. By modifying the cellular or tissue location of the foreign gene, the function of the biologically active polymer can be enhanced. The cell targeting signal can be, but is not limited to, a protein, peptide, lipid, steroid, sugar, carbohydrate, (non-expressing) polynucleic acid or synthetic compound. Cell targeting signals such as ligands enhance cellular binding to receptors. A variety of ligands have been used to target drugs and genes to cells and to specific cellular receptors. The ligand may seek a target within the cell membrane, on the cell membrane or near a cell. Binding of ligands to receptors typically initiates endocytosis. Ligands include agents that target to the asialoglycoprotein receptor by using asialoglycoprotein or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting.

Other targeting groups include molecules that interact with membranes such as lipids, fatty acids, cholesterol, dansyl compounds, and amphotericin derivatives. In addition viral proteins could be used to bind cells.

After interaction of a compound or complex with the cell, other targeting groups can be used to increase the delivery of the biologically active polymer to certain parts of the cell.

Nuclear localizing signals enhance the targeting of the pharmaceutical into proximity of the nucleus and/or its entry into the nucleus during interphase of the cell cycle. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. Other NLS peptides have been derived from the hnRNP A1 protein, nucleoplasmin, c-myc, etc.

Many biologically active polymers, in particular large and/or charged compounds, are incapable of crossing biological membranes. In order for these compounds to enter cells, the cells must either take them up by endocytosis, i.e., into endosomes, or there must be a disruption of the cellular membrane to allow the compound to cross. In the case of endosomal entry, the endosomal membrane must be disrupted to allow for movement out of the endosome and into the cytoplasm. Either entry pathway into the cell requires a disruption or alteration of the cellular membrane. Compounds that disrupt membranes or promote membrane fusion are called membrane active compounds. These membrane active compounds, or releasing signals, enhance release of endocytosed material from intracellular compartments such as endosomes (early and late), lysosomes, phagosomes, vesicle, endoplasmic reticulum, Golgi apparatus, trans Golgi network (TGN), and sarcoplasmic reticulum. Release includes movement out of an intracellular compartment into the cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides. The control of when and where the membrane active compound is active is crucial to effective transport. If the membrane active agent is operative in a certain time and place it would facilitate the transport of the biologically active polymer across the biological membrane. If the membrane active compound is too active or active at the wrong time, then no transport occurs or transport is associated with cell rupture and cell death. Nature has evolved various strategies to allow for membrane transport of biologically active polymers including membrane fusion and the use of membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

Another functional group comprises compounds, such as polyethylene glycol, that decrease interactions between molecules and themselves and with other molecules. Such groups are useful in limiting interactions such as between serum factors and the molecule or complex to be delivered.

By delivered we mean that the polynucleotide or other biologically active polymer becomes associated with the cell. The polynucleotide or other biologically active polymer can be on the membrane of the cell or inside the cytoplasm, nucleus, or other organelle of the cell. The process of delivering a nucleic acid to a cell has been commonly termed transfection or the process of transfecting and also it has been termed transformation. The term transfecting as used herein refers to the introduction of foreign nucleic acid or other biologically active polymer into cells. The biologically active polymer could be used for research purposes or to produce a change in a cell that can be therapeutic. The delivery of nucleic acid for therapeutic purposes is commonly called gene therapy. The delivery of nucleic acid can lead to modification of the genetic material present in the target cell. The term stable transfection or stably transfected generally refers to the introduction and integration of exogenous nucleic acid into the genome of the transfected cell. The term stable transfectant refers to a cell which has stably integrated foreign nucleic acid into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of foreign nucleic acid into a cell where the foreign nucleic acid does not integrate into the genome of the transfected cell. A biologically active polymer is a compound having the potential to react with biological components. Pharmaceuticals, proteins, peptides, hormones, cytokines, antigens and nucleic acids are examples of biologically active polymers. These processes can be used for transferring nucleic acids or biomolecules into cells or an organism such as for drug delivery, or may also be used for analytical methods.

A delivery system is the means by which a biologically active polymer becomes delivered. That is all compounds, including the biologically active polymer itself, that are required for delivery and all procedures required for delivery including the form (such volume and phase (solid, liquid, or gas)) and method of administration (such as but not limited to oral or subcutaneous methods of delivery).

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, β-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The term polynucleotide includes deoxyribonucleic acid (DNA) and ribonucleic acid (RNA) and combinations on DNA, RNA and other natural and synthetic nucleotides.

DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15-50 base pairs and preferably 21-25 base pairs and having a nucleotide sequence identical or nearly identical to an expressed target gene or RNA within the cell. Interference may result in suppression of expression. The polynucleotide can be a sequence whose presence or expression in a cell alters the expression or function of cellular genes or RNA. In addition, DNA and RNA may be single, double, triple, or quadruple stranded. Double, triple, and quadruple stranded polynucleotide may contain both RNA and DNA or other combinations of natural and/or synthetic nucleic acids.

A delivered polynucleotide can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. Polynucleotides may contain an expression cassette coded to express a whole or partial protein, or RNA. An expression cassette refers to a natural or recombinantly produced polynucleotide that is capable of expressing a gene(s). The term recombinant as used herein refers to a polynucleotide molecule that is comprised of segments of polynucleotide joined together by means of molecular biological techniques. The cassette contains the coding region of the gene of interest along with any other sequences that affect expression of the gene. A DNA expression cassette typically includes a promoter (allowing transcription initiation), and a sequence encoding one or more proteins. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences.

The polynucleotide may contain sequences that do not serve a specific function in the target cell but are used in the generation of the polynucleotide. Such sequences include, but are not limited to, sequences required for replication or selection of the polynucleotide in a host organism.

A polynucleotide can be used to modify the genomic or extrachromosomal DNA sequences. This can be achieved by delivering a polynucleotide that is expressed. Alternatively, the polynucleotide can effect a change in the DNA or RNA sequence of the target cell. This can be achieved by hybridization, multistrand polynucleotide formation, homologous recombination, gene conversion, or other yet to be described mechanisms.

The term gene generally refers to a polynucleotide sequence that comprises coding sequences necessary for the production of a therapeutic polynucleotide (e.g., ribozyme) or a polypeptide or precursor. The polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses the coding region of a gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term gene encompasses both cDNA and genomic forms of a gene. A genomic form or clone of a gene contains the coding region interrupted with non-coding sequences termed introns, intervening regions or intervening sequences. Introns are segments of a gene which are transcribed into nuclear RNA. Introns may contain regulatory elements such as enhancers. Introns are removed or spliced out from the nuclear or primary transcript; introns therefore are absent in the messenger RNA (mRNA) transcript. The mRNA functions during translation to specify the sequence or order of amino acids in a nascent polypeptide. The term non-coding sequences also refers to other regions of a genomic form of a gene including, but not limited to, promoters, enhancers, transcription factor binding sites, polyadenylation signals, internal ribosome entry sites, silencers, insulating sequences, matrix attachment regions. These sequences may be present close to the coding region of the gene (within 10,000 nucleotide) or at distant sites (more than 10,000 nucleotides). These non-coding sequences influence the level or rate of transcription and translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, and immunogenicity. One example of covalent modification of nucleic acid involves the action of LabelIT reagents (Mirus Corporation, Madison, Wis.).

As used herein, the term gene expression refers to the process of converting genetic information encoded in a gene into RNA (e.g., mRNA, rRNA, tRNA, or snRNA) through transcription of a deoxyribonucleic gene (e.g., via the enzymatic action of an RNA polymerase), and for protein encoding genes, into protein through translation of mRNA. Gene expression can be regulated at many stages in the process. Up-regulation or activation refers to regulation that increases the production of gene expression products (i.e., RNA or protein), while down-regulation or repression refers to regulation that decrease production. Molecules (e.g., transcription factors) that are involved in up-regulation or down-regulation are often called activators and repressors, respectively.

A biologically active polymer is a compound having the potential to react with biological components. More particularly, biologically active polymers utilized in this specification are designed to change the natural processes associated with a living cell. For purposes of this specification, a cellular natural process is a process that is associated with a cell before delivery of a biologically active polymer. Biologically active polymers may be selected from the group comprising: pharmaceuticals, proteins, peptides, polypeptides, hormones, cytokines, antigens, viruses, oligonucleotides, and nucleic acids or polynucleotides.

EXAMPLES

Example 1

Formation of an Imidazolinium Containing Copolymer.

Linear polyethylenimine with N-propionyl substitution (10% of the amines acylated, 90% ethylamine by 1H NMR, Polysciences, Inc., 1H NMR ($D_2O$, 3-(trimethylsilyl)propionic-2,2,3,3-d4 acid sodium salt as an internal reference) $\delta 3.65$-$3.45$, m, 6 H; $\delta 3.15$-$2.80$, m, 47 H; $\delta 2.46$, q, 2H; $\delta 1.09$, t, 3H) was dissolved in water to a concentration of 20 mg/mL. The pH of the solution was adjusted to pH 5.0 with hydrochloric acid (12 M). The solution was split into two portions. One portion was placed at 4° C. for 48 h. The second portion was placed at 37° C. for 48 h. The size exclusion profile for each sample was obtained (250 µg in 250 µL Hepes Buffered Saline, BioCad-Sprint, Perseptive Biosystems, Inc., Eichrome Technologies Columns, SPCCS201-30 and SPCCS203-30 connected in series, 0.2 M NaCl eluent, monitored at $\lambda 210$ and $\lambda 240$). The traces for the samples were essentially identical, indicating that the molecular weight of the polymer was not effected by the process. The only difference noted in the example was that the 37° C. sample had a much higher absorbance at $\lambda 240$. The UV spectra for each sample was run (0.2 mg/mL in $H_2O$, $\lambda$ 190 nm-300 nm). The sample stored at 4° C. exhibited a $\lambda$max at 205 nm, which was identical to the reaction starting material (starting material not shown). The sample kept at 37° C. exhibited a $\lambda$max at 235 nm. The IR spectra for each sample showed very similar signals, with slight differences in the 1240-1300 $cm^{-1}$ region and in the 1550-1640 $cm^{-1}$ region. 1H NMR analysis indicated ($D_2O$, 3-(trimethylsilyl)propionic-2,2,3,3-d4 acid sodium salt as an internal reference) $\delta 3.91$, s, 8.2H; $\delta 3.65$-$3.45$, m, 15.6 H; $\delta 3.15$-$2.80$, m, 131 H; $\delta 2.66$, q, 4.4H; $\delta 2.46$, q, 2H; $\delta 1.22$, t, 7.6 H; $\delta 1.09$, t, 3H. The new signals at $\delta 3.91$, $\delta 2.66$, and $\delta 1.22$ are consistent for the imidazolinium ring system. The 1H NMR supports the assignment of 3.3% of the amines acylated, 7.26% imidazolinium, 89.1% ethylamine. These results show that the original ethylamine sections remain and that the new ring system arises with a corresponding decrease in the amide.

Example 2

In Vivo Mouse Injections of Polyimidazolinium Formulations for Lung Transfection.

The same samples generated in Example 1 were formulated into DNA-containing preparations for intravenous systemic gene transfer. Two complexes were formed. Complex I. pDNA (50 µg, 25 µL of a 2 µg/µL solution in water) was diluted with 10 mM HEPES, 0.29 M glucose, pH 7.5 (200 µL). To this solution was added the 4° C. sample (400 µg, 20 µL of a 20 mg/mL solution in water). To this solution was added polyacrylic acid (50 µg, 5 µL of a 10 mg/mL solution in water). Complex II. pDNA (50 µg, 25 µL of a 2 µg/µL solution in water) was diluted with 10 mM HEPES, 0.29 M glucose, pH 7.5 (200 µL). To this solution was added the 37° C. sample (400 µg, 20 µL of a 20 mg/mL solution in water). To this solution was added polyacrylic acid (50 µg, 5 µL of a 10 mg/mL solution in water).

Tail vein injections of 250 µL of the complex were preformed on ICR mice (Complex I, n=4; Complex II, n=3) using a 30 gauge, 0.5 inch needle. 30 min post injection, the animals were injected with polyacrylic acid (1500 µg, 150 µL of a 10 mg/mL solution in water). One day after injection, the animals were sacrificed, and luciferase assays were conducted on the lung samples. Luciferase expression was determined as previously reported (Wolff et al. 1990). A Lumat L B 9507 (EG&G Berthold, Bad-Wildbad, Germany) luminometer was used. The results, indicate that the polyimidazolinium complex is more efficient at gene transfer to lung than the linear polyethylenimine with 10% N-propionyl substitution.

Example 3 pH Effect on the Formation of an Imidazolinium Containing Copolymer.

Linear polyethylenimine with N-propionyl substitution (10% of the amines acylated, 90% ethylamine by 1H NMR, Polysciences, Inc.) was dissolved in water to a concentration of 20 mg/mL, and the pH was adjusted to 7.4. From this stock, two samples were prepared, one in which the pH was raised to 8, and a second sample with a pH of 5. The samples were heated to 37° C. for 64 h and analyzed by UV spectroscopy. The UV spectra for each sample was run (0.2 mg/mL in $H_2O$, $\lambda$ 190 nm-300 nm). The sample stored pH 5 showed the largest increase in absorbance at $\lambda 235$-240. The pH 8 sample also showed an increase in absorbance at $\lambda 235$-240, indicating that the cyclization takes place above pH 8.

Example 4

Alkylation of N,N'-Dimethylethylenediamine with Propionyl Chloride. Synthesis of MC1016 (Monoaddition) and MC1017 (Diaddition).

N,N'-Dimethylethylenediamine (500 mg, 11.3 mmol amine, Aldrich Chemical Company) was transferred to a flame dried round bottom flask and taken up with dichloromethane (100 mL, 0.1 M). To the resulting solution was added diisopropylethylamine (0.99 mL, 730 mg, 5.67 mmol, Aldrich Chemical Company) and the solution was stirred at RT under $N_2$. The reaction mixture was cooled in a dry ice/acetone bath. Propionyl chloride (0.49 mL, 525 mg, 5.67 mmol, Aldrich Chemical Company) was added dropwise over 5 min to the reaction solution with stirring. The reaction was allowed to warm to RT with stirring, under $N_2$. After 30 min at RT, the reaction mixture was analyzed by TLC and mass spectroscopy (Sciex API 150EX) to verify that the reaction was complete. The mixture was concentrated under reduced pressure, and a portion (100 mg) was brought up in $H_2O$. This solution was purified by HPLC (Aquasil C18 column, 0.1% $TFA/H_2O$ and 0.1% TFA/MeCN eluent with a 10-90% (organic) gradient over 20 min, elution rate of 1 mL/min, fractions were collected at 210 nm). Fractions 1-6 (from two runs) were concentrated under reduced pressure, and lyophilized to afford monopropionylated N'N-dimethylethylenediamine as a white solid (MC1016, 91.7 mg, as analyzed by mass spectroscopy (Sciex API 150EX). Fraction 10 (from two runs) was concentrated under reduced pressure, and lyophilized to afford N,N'-dipropionylated N,N'-dimethylethylenediamine as a white solid (MC1017, 7.8 mg, analyzed by mass spectroscopy (Sciex API 150EX).

Example 5

Synthesis of 1,3-Dimethy, 2-Ethyl Imidazolinium Chloride.

Monopropionylated N'N-dimethylethylenediamine (MC1016) was taken up in water to a final concentration of 20 mg/mL. The pH of the solution was adjusted to pH 5 with concentrated HCl. The resulting solution was heated at 70° C. for 72 h. The sample was analyzed by UV Spectroscopy. Analysis indicated an increase in the absorption at $\lambda 210$ nm for the heated solution relative to a sample stored at 4° C.

Example 6

Synthesis of and Amidinium Formation from Monoacylated Pentaethylenehexamine.

Pentaethylenehexamine (10 mg, 0.043 mmol, Aldrich Chemical Company) was taken up in dichloromethane (1 mL). The solution was cooled in an ice bath under nitrogen, and acetyl chloride (3.4 mg, 0.043 mmol, Aldrich) was added. The solution was allowed to warm to ambient temperature and concentrated under reduced pressure. The resulting oil was taken up in water at a concentration of 20 mg/mL, and the pH was adjusted to 7 with HCl (6 M). The sample was divided into two portions. Sample 1 was left at RT while sample 2 was heated at 80° C. After 48 h, the samples were analyzed by UV spectroscopy (Beckman DU530 Spectrophotometer. The results indicate an increased absorbance at 230-235 for both the RT and the 80° C. samples.

Example 7

Mouse In Vivo Injections of Polyimidazolinium Formulations for Lung Transfection.

Three samples of polyimidazolinium were prepared from poly(2-ethyl-2-oxazoline) that was 90% deamidated (PolySciences), by dissolving the polymer at 20 mg/mL in water, adjusting the to pH 7.4, and carrying out cyclization by incubation at elevated temperature. Polyimidazolinium 1 was prepared 6 weeks before use, and was allowed to sit at RT. Polyimidazolinium 2 was prepared 4 weeks before use, and was allowed to sit at RT. Polyimidazolinium 3 was prepared immediately prior to use. The three polyimidazolinium preparations were analyzed by UV spectroscopy ($\lambda$190 nm-300 nm. Polyimidazolinium 1 showed a large increase in absorbance at $\lambda 235$, whereas for Polyimidazolinium 2, this peak was present, but at a lower amount. Polyimidazolinium did not show a $\lambda 235$ absorbance. The three polyimidazolinium preparations were used to make several complexes.

Complex I. pDNA (150 µg, 75 µL of a 2 µg/µL solution in water) was diluted with 10 mM HEPES, 0.29 M glucose, pH 7.5 (600 µL). To this solution was added polyimidazolinium 1 (1200 µg, 60 µL of a 20 mg/mL solution in water). To this solution was added polyacrylic acid (150 µg, 15 µL of a 10 mg/mL solution in water). Complex II. pDNA (150 µg, 75 µL of a 2 µg/µL solution in water) was diluted with 10 mM HEPES, 0.29 M glucose, pH 7.5 (600 µL). To this solution was added polyimidazolinium 2 (1200 µg, 60 µL of a 20 mg/mL solution in water. To this solution was added polyacrylic acid (150 µg, 15 µL of a 10 mg/mL solution in water). Complex III. pDNA (150 µg, 75 µL of a 2 µg/µL solution in water) was diluted with 10 mM HEPES, 0.29 M glucose, pH 7.5 (600 µL). To this solution was added polyimidazolinium 3 (1200 µg, 60 µL of a 20 mg/mL solution in water. To this solution was added polyacrylic acid (150 µg, 15 µL of a 10 mg/mL solution in water).

Tail vein injections of 250 µL of the complex were performed on ICR mice (n=3) using a 30 gauge, 0.5 inch needle. 30 min post injection, the animals were injected with polyacrylic acid (1500 µg, 150 µL of a 10 mg/mL solution in water). One day after injection, the animals were sacrificed, and a luciferase assay was conducted on the lung tissue. A Lumat LB 9507 (EG&G Berthold, Bad-Wildbad, Germany) luminometer was used. The results are summarized in the table below.

| Complex | Relative Luciferase Activity (light units) | | |
| --- | --- | --- | --- |
| | n1 | n2 | n3 |
| Complex I | 4,231,357 | 2,280,870 | 4,933,875 |
| Complex II | 2,671,040 | 2,525,587 | 1,186,365 |
| Complex III | 1,774,820 | 878,562 | 2,969,813 |

The results indicate that the polyimidazolinium formulations deliver pDNA to the lung.

Example 8

Transfection of 3T3 Cells with Polyimidazolinium Formulations.

Several Complexes were formed for cell transfections. Linear polyethylenimine with N-propionyl substitution (10% of the amines acylated, 90% ethylamine by 1H NMR, Polysciences, Inc., lPEI110% NPr was dissolved in water to a concentration of 20 mg/mL. The pH of the solution was adjusted to pH 7.5 with hydrochloric acid (12 M). The polyimidazolinium derived from this polymer was also utilized in complex formation.

3T3 cells were maintained in DMEM. Approximately 24 h prior to transfection, cells were plated at an appropriate density in 48-well plates and incubated overnight. Cultures were maintained in a humidified atmosphere containing 5% $CO_2$ at 37° C. The indicated amount of complex was then combined with the cells in 1 mL media. Cells were harvested after 24 h and assayed for luciferase activity using a Lumat LB 9507 (EG&G Berthold, Bad-Wildbad, Germany) luminometer. The amount of luciferase expression was recorded in relative light units. Numbers are the average for two separate wells.

| | Sample | complex | W:W Ratio | µL/ Well | Average RLU |
|---|---|---|---|---|---|
| 1 | pDNA | lPEI10% NPr | 5/5 | 40 | 416,992 |
| 2 | pDNA | lPEI10% NPr | 5/10 | 40 | 1,292,181 |
| 3 | pDNA | lPEI10% NPr | 5/15 | 40 | 1,298,805 |
| 4 | pDNA | lPEI10% NPr | 5/20 | 40 | 1,369,775 |
| 5 | pDNA | lPEI10% NPr | 5/30 | 40 | 1,511,175 |
| 6 | pDNA | lPEI10% NPr | 5/40 | 40 | 1,067,322 |
| 7 | pDNA | Polyimidazolinium | 5/5 | 40 | 155,842 |
| 8 | pDNA | Polyimidazolinium | 5/10 | 40 | 331,081 |
| 9 | pDNA | Polyimidazolinium | 5/15 | 40 | 420,084 |
| 10 | pDNA | Polyimidazolinium | 5/20 | 40 | 281,017 |
| 11 | pDNA | Polyimidazolinium | 5/30 | 40 | 1,037,222 |
| 12 | pDNA | Polyimidazolinium | 5/40 | 40 | 1,067,404 |

The results indicate that the polyimidazolinium is able to transfect 3T3 cells at a lower efficiency than lPEI1 10% NPr under these conditions. The lPEI1 10% NPr showed a similar toxicity profile (as judged by the final confluency) to the polyimidazolinium polymer.

Example 9

Transfection of HUH-7 Cells with Recharged Polyimidazolinium Formulations.

Linear polyethylenimine with N-propionyl substitution (10% of the amines acylated, 90% ethylamine by 1H NMR, Polysciences, Inc.), was dissolved in water to a concentration of 20 mg/mL. The pH of the solution was adjusted to pH 7.5 with hydrochloric acid (12 M), and the polyimidazolinium (PI) was formed at elevated temperature. The samples were recharged with various amounts of polyacrylic acid (10 mg/mL solution in water).

HUH-7 cells were maintained in DMEM. Approximately 24 h prior to transfection, cells were plated at an appropriate density in 48-well plates and incubated overnight. Cultures were maintained in a humidified atmosphere containing 5% CO2 at 37° C. The indicated amount of complex was then combined with the cells in 1 mL of media. Cells were harvested after 24 h and assayed for luciferase activity using a Lumat LB 9507 (EG&G Berthold, Bad-Wildbad, Germany) luminometer. The amount of luciferase expression was recorded in relative light units. Numbers are the average for two separate wells.

Transfection of HUH7 cell using DNA/polyimidazolinium (PI)/polyacrylic acid complexes.

| Complex | W:W Ratio | µL/ Well | Media | Average RLU |
|---|---|---|---|---|
| pDNA/PI/PAA | 5/20/0 | 40 | Opti | 3981083 |
| pDNA/PI/PAA | 5/20/14 | 40 | Opti | 13111775 |
| pDNA/PI/PAA | 5/20/16 | 40 | Opti | 12334305 |
| pDNA/PI/PAA | 5/20/18 | 40 | Opti | 11000786 |
| pDNA/PI/PAA | 5/20/19 | 40 | Opti | 11458729 |
| pDNA/PI/PAA | 5/20/20 | 40 | Opti | 10099756 |
| pDNA/PI/PAA | 5/20/21 | 40 | Opti | 7820030 |

-continued

Transfection of HUH7 cell using DNA/polyimidazolinium (PI)/polyacrylic acid complexes.

| Complex | W:W Ratio | µL/ Well | Media | Average RLU |
|---|---|---|---|---|
| pDNA/PI/PAA | 5/20/22 | 40 | Opti | 504225 |
| pDNA/PI/PAA | 5/20/0 | 40 | Serum | 2197 |
| pDNA/PI/PAA | 5/20/14 | 40 | Serum | 544564 |
| pDNA/PI/PAA | 5/20/16 | 40 | Serum | 3165930 |
| pDNA/PI/PAA | 5/20/18 | 40 | Serum | 8597630 |
| pDNA/PI/PAA | 5/20/19 | 40 | Serum | 7959588 |
| pDNA/PI/PAA | 5/20/20 | 40 | Serum | 6975200 |
| pDNA/PI/PAA | 5/20/21 | 40 | Serum | 6504250 |
| pDNA/PI/PAA | 5/20/22 | 40 | Serum | 36167 |

The results indicate that recharged polyimidazolinium formulations are effective in transfecting HUH-7 cells.

Example 10

Transfection of HUH-7 Cells with Binary and Ternary Polyimidazolinium Formulations.

Linear polyethylenimine with N-propionyl substitution (lPEI10% NPr, 10% of the amines acylated, 90% ethylamine by 1H NMR, Polysciences, Inc.), was dissolved in water to a concentration of 20 mg/mL. The pH of the solution was adjusted to pH 7.5 with hydrochloric acid (12 M). A portion of this solution was used to form the polyimidazolinium (PI) by holding the solution at elevated temperature. The samples were recharged with various amounts of polyacrylic acid (10 mg/mL solution in water). HUH-7 cells were maintained in DMEM. Approximately 24 h prior to transfection, cells were plated at an appropriate density in 48-well plates and incubated overnight. Cultures were maintained in a humidified atmosphere containing 5% CO2 at 37° C. The indicated amount of complex was then combined with the cells in 1 mL of media. Cells were harvested after 24 h and assayed for luciferase activity using a Lumat LB 9507 (EG&G Berthold, Bad-Wildbad, Germany) luminometer. The amount of luciferase expression was recorded in relative light units. Numbers are the average for two separate wells.

| complex | W:W Ratio | µL/ Well | Average RLU | Final Confluency: |
|---|---|---|---|---|
| DNA/PI/PAA | 5/10/0 | 40 | 4292994 | 100 |
| DNA/PI/PAA | 5/20/0 | 40 | 3282018 | 85 |
| DNA/PI/PAA | 5/40/0 | 40 | 3477386 | 85 |
| DNA/PI/PAA | 5/60/0 | 40 | 3233045 | 75 |
| DNA/PI/PAA | 5/40/25 | 40 | 8530972 | 75 |
| DNA/PI/PAA | 5/40/30 | 40 | 7066358 | 75 |
| DNA/PI/PAA | 5/40/35 | 40 | 6675965 | 85 |
| DNA/PI/PAA | 5/40/40 | 40 | 6669150 | 85 |
| DNA/lPEI10% NPr/PAA | 5/10/0 | 40 | 1895920 | 90 |
| DNA/lPEI10% NPr/PAA | 5/20/0 | 40 | 3881579 | 85 |
| DNA/lPEI10% NPr/PAA | 5/40/0 | 40 | 5655288 | 60 |
| DNA/lPEI10% NPr/PAA | 5/60/0 | 40 | 431360 | 60 |
| DNA/lPEI10% NPr/PAA | 5/40/25 | 40 | 2390180 | 60 |
| DNA/lPEI10% NPr/PAA | 5/40/30 | 40 | 6709513 | 60 |
| DNA/lPEI10% NPr/PAA | 5/40/35 | 40 | 8483672 | 65 |
| DNA/lPEI10% NPr/PAA | 5/40/40 | 40 | 7779514 | 65 |

The results indicate that the polyimidazolinium polymer is effective at transfecting HUH-7 cells either as a binary or a ternary, recharged complex. The results indicate that the

Example 11

Methylation of 2-Methyl-2-Imidazoline.

To a solution of 2-methyl-2-imidazoline (52.7 mg, 0.626 mmol, Aldrich Chemical Company) in 3 mL acetonitrile was added methyl iodide (86 μL, 1.377 mmol, Aldrich Chemical Company). The resulting solution was heated to reflux. After 3 days, the solution was removed from heat, and diethyl ether was added to precipitate the salts. The resulting precipitate was dried under vacuum. The material was analyzed by mass spectroscopy (Sciex API 150EX) and indicated a mixture of 1,2-dimethyl imidazolinium iodide (M=99), 1,2,3-trimethyl imidazolinium iodide (M=113), and 1,1,4-trimethyl, 4-acyl-ethylenediamine (M+1=145). The mixture was analyzed by UV spectroscopy (Beckman DU530 Spectrophotometer), and indicated a shift in λmax from 214 nm to 224 nm for the imidazolinium iodide sample relative to the starting imidazoline.

Example 12

Polymerization of 2-Methyl-2-Imidazoline and 1,4-Butanediol Diglycidyl Ether.

To a solution of 2-methyl-2-imidazoline (200 mg, 2.38 mmol, Aldrich Chemical Company) in 5 mL DMF was added 1,4-Butanediol diglycidyl ether (458 μL, 2.38 mmol, Aldrich Chemical Company). The solution was heated at reflux for 1.5 h, and the resulting polymer gel was washed with diethylether. The mixture was analyzed by UV spectroscopy (Beckman DU530 Spectrophotometer), and indicated a shoulder absorbance of λ 235 nm for the imidazolinium polymer, indicating incorporation of the ring system into the polymer.

Example 13

Polymerization of 2-Methyl-2-Imidazoline and Epichlorohydrine.

To a solution of 2-methyl-2-imidazoline (200 mg, 2.38 mmol, Aldrich Chemical Company) in 5 mL DMF was added epichlorohydrine (186 μL, 2.38 mmol, Aldrich Chemical Company). The solution was heated at reflux for 16 h, and the resulting polymer was precipitated with diethylether. The precipitate was analyzed by UV spectroscopy (Beckman DU530 Spectrophotometer), and indicated an absorbance of λ 235 nm for the imidazolinium polymer, indicating incorporation of the ring system into the polymer.

Example 14

Polymerization of 2-Methyl-2-Imidazoline and Polyepichlorohydrine.

To a solution of polyepichlorohydrine (102.9 mg, 1.48 mmol in Cl,) in 2 mL acetonitrile, was added 2-methyl-2-imidazoline (125 mg, 1.48 mmol, Aldrich Chemical Company). The solution was heated at reflux for 16 h, and the resulting polymer was precipitated with diethylether. The precipitate was analyzed by UV spectroscopy (Beckman DU530 Spectrophotometer), and indicated a new shoulder absorbance of λ 220 nm for the imidazolinium polymer, indicating incorporation of the ring system into the polymer.

Example 15

Partial Deprotections of 2-Ethyl-2-Oxazoline.

A. To a solution of 2-ethyl-2-oxazoline (5.00 g, 50.4 mmol in amide, Aldrich Chemical Company) in 40 mL of water was added HCl (conc, 2.05 mL, 25.2 mmol, 0.5 eq) dropwise over several minutes. The resulting solution was heated at reflux for 56 h. The pH was neutralized to pH 7 with NaOH (12 M). The solution was concentrated under reduced pressure and taken up in EtOH and filtered to remove NaCl. The ethanol filtration was repeated 5 times to afford a copolymer of the following subunits: ethyl amine, 2-ethylimidazolinium, and N-propionyl-ethyl amine. The ratios of the subunits were determined by 1H NMR to be 88.9%, 4.9%, and 6.2% respectively.

B. To a solution of 2-ethyl-2-oxazoline (5.00 g, 50.4 mmol in amide, Aldrich Chemical Company) in 40 mL of water was added HCl (con, 2.67 mL, 32.8 mmol, 0.65 eq) dropwise over several minutes. The resulting solution was heated at reflux for 56 h. The pH was neutralized to pH 7 with NaOH (12 M). The solution was concentrated under reduced pressure and taken up in EtOH and filtered to remove NaCl. The ethanol filtration was repeated 5 times to afford a copolymer of the following subunits: ethyl amine, 2-ethylimidazolinium, and N-propionyl-ethyl amine. The ratios of the subunits were determined by 1H NMR to be 92.8%, 4%, and 3.2% respectively.

C. To a solution of 2-ethyl-2-oxazoline (5.00 g, 50.4 mmol in amide, Aldrich Chemical Company) in 40 mL of water was added HCl (con, 3.48 mL, 42.8 mmol, 0.85 eq) dropwise over several minutes. The resulting solution was heated at reflux for 56 h. The pH was neutralized to pH 7 with NaOH (12 M). The solution was concentrated under reduced pressure and taken up in EtOH and filtered to remove NaCl. The ethanol filtration was repeated 5 times to afford a copolymer of the following subunits: ethyl amine, 2-ethylimidazolinium, and N-propionyl-ethyl amine. The ratios of the subunits were determined by 1H NMR to be 95%, 3.35%, and 1.65% respectively.

D. To a solution of 2-ethyl-2-oxazoline (5.00 g, 50.4 mmol in amide, Aldrich Chemical Company) in 40 mL of water was added HCl (con, 6.14 mL, 75.6 mmol, 1.5 eq) dropwise over several minutes. The resulting solution was heated at reflux for 48 h. The pH was neutralized, than made basic, to pH 14 with NaOH (12 M). The solution was heated at reflux for 16 h. After 16 h, the pH was neutralized to pH 7 with HCl (con). The solution was concentrated under reduced pressure and taken up in EtOH and filtered to remove NaCl. The ethanol filtration was repeated 5 times to afford a copolymer of the following subunits: ethyl amine, 2-ethylimidazolinium, and N-propionyl-ethyl amine. The ratios of the subunits were determined by 1H NMR to be 100%, 0%, and 0% respectively.

E. To a solution of 2-ethyl-2-oxazoline (5.00 g, 50.4 mmol in amide, Aldrich Chemical Company) in 40 mL of water was added NaOH (3.024 g, 75.6 mmol, Aldrich Chemical Company) portion wise over several minutes. The polymer started to drop out as the pH increased. The resulting suspension was heated at reflux for 56 h. The pH was neutralized to pH 7 with HCl (con). The solution was concentrated under reduced pressure and taken up in EtOH and filtered to remove NaCl. The ethanol filtration was repeated 5 times to afford a copolymer of the following subunits: ethyl amine, 2-ethylimidazolinium, and N-propionyl-ethyl amine. The ratios of the subunits were determined by 1H NMR to be a trace %, a trace %, and 98% respectively.

Example 16

Acylation of Polyvinyl Amine and the Formation of an Amidinium Ring.

To a solution of polyvinyl amine hydrochloride (40 mg, 0.503 mmol in amine, 25 K, Aldrich Chemical Company) in 400 μL water was added diisopropylethylamine (35 μL, 1.00 mmol, Aldrich Chemical Company), followed by acetic anhydride (9.6 μL, 0.503 mmol, Aldrich Chemical Company). The resulting solution was stirred for 12 h, and split into two equal sized portions. Sample 1 (MC 1025) was heated at 70° C. for 16 h. Sample 2 (MC1026) was stored at 4° C.

Example 17

Acylation of Polyallylamine and the Formation of an Amidinium Ring.

To a solution of polyallylamine hydrochloride (40 mg, 0.428 mmol in amine, 15 K, Aldrich Chemical Company) in 400 μL water was added diisopropylethylamine (30 μL, 0.855 mmol, Aldrich Chemical Company), followed by acetic anhydride (8.1 μL, 0.428 mmol, Aldrich Chemical Company). The resulting solution was stirred for 12 h, and split into two equal sized portions. Sample 1 (MC 1029) was heated at 70° C. for 16 h. Sample 2 (MC1030) was stored at 4° C.

Example 18

Delivery of siRNA to Cells In Vitro.

Several complexes were prepared for in vitro transfection of 3T3-Luc cell. Some formulations include a lipid (MC 798), while others are lipid free. Transfections were conducted in 10% serum. 3T3-Luc cells were maintained in DMEM. Approximately 24 h prior to transfection, cells were plated at an appropriate density in 48-well plates and incubated overnight. Cultures were maintained in a humidified atmosphere containing 5% $CO_2$ at 37° C. The indicated amount of complex containing anti-luciferase siRNA (GL-2) and the indicated polymer was then combined with the cells in 1 mL of media. Cells were harvested after 24 h and assayed for luciferase activity using a Lumat LB 9507 (EG&G Berthold, Bad-Wildbad, Germany) luminometer. The amount of luciferase expression was recorded in relative light units. Numbers are the average for two separate wells.

Cell type: 3T3-Luc

| Sample | Formulation | Concentration w:w ratio | μL/Well | RLU |
|---|---|---|---|---|
| Blank | X | | 100 | 2100570 |
| GL-2 | X | 200 | 100 | 1976795 |
| GL-2 | TKO | 200/8 uL | 100 | 1094425 |
| GL-2 | TKO | 200 ng/12 μL | 100 | 517800 |
| GL-2 | PVA control | 200 ng/6 μL | 100 | 1952695 |
| GL-2 | 1025 | 200 ng/6 μL | 100 | 1480135 |
| GL-2 | 1026 | 200 ng/6 μL | 100 | 1539960 |
| GL-2 | PAA control | 200 ng/6 μL | 100 | 1711830 |
| GL-2 | 1029 | 200 ng/6 μL | 100 | 1554965 |
| GL-2 | 1030 | 200 ng/6 μL | 100 | 1585145 |
| GL-2/798 | PVA control | 200 ng/4 μg/6 μL | 100 | 1829290 |
| GL-2/798 | 1025 | 200 ng/4 μg/6 μL | 100 | 1432655 |
| GL-2/798 | 1026 | 200 ng/4 μg/6 μL | 100 | 1511445 |
| GL-2/798 | PAA control | 200 ng/4 μg/6 μL | 100 | 1610610 |
| GL-2/798 | 1029 | 200 ng/4 μg/6 μL | 100 | 1404530 |
| GL-2/798 | 1030 | 200 ng/4 μg/6 μL | 100 | 1840955 |

The results indicate that the siRNA can be delivered to cells using the indicated polymers thus inhibiting expression of the luciferase gene.

Example 19

Delivery of DNA to Cells In Vitro.

Several complexes were prepared for in vitro transfection of HEPA cells. The formulations include a lipid (MC 798). Transfections were conducted in 10% serum. HEPA cells were maintained in DMEM. Approximately 24 h prior to transfection, cells were plated at an appropriate density in 48-well plates and incubated overnight. Cultures were maintained in a humidified atmosphere containing 5% $CO_2$ at 37° C. The indicated amount of complex was then combined with the cells in 1 mL of media. Cells were harvested after 24 h and assayed for luciferase activity using a Lumat LB 9507 (EG&G Berthold, Bad-Wildbad, Germany) luminometer. The amount of luciferase expression was recorded in relative light units. Numbers are the average for two separate wells.

Cell type: HEPA

| polymer | concentration w:w:w ratio (DNA/lipid/polymer) | RLU |
|---|---|---|
| pAA | 3/9/6 | 347944 |
| pAA | 3/15/6 | 1060816 |
| 1029 | 3/9/6 | 2942677 |
| 1029 | 3/15/6 | 7128621 |
| 1030 | 3/9/6 | 2857683 |
| 1030 | 3/15/6 | 2821997 |
| 1029 | 3/9/12 | 2597371 |

The results indicate that the polyamidinium polymer is able to transfer DNA to cells in vitro.

The foregoing is considered as illustrative only of the principles of the invention.

Furthermore, since numerous modifications and changes will readily occur to those skilled in the art, it is not desired to limit the invention to the exact construction and operation shown and described. Therefore, all suitable modifications and equivalents fall within the scope of the invention.

REFERENCES

Adam R C, K G Rice. J Pharm Sci. 739-746, 1999.
Anderson M W, Jones R C F. *J Chem Soc Perkin Trans. 1*, 1986, 205.
Askitoglu. Helv Chim Acta 1985, 68:750.
Barnett C, Cleghorn P H, Cross G E, Lloyd D, Marshall R. *J Chem Soc C*, 1966, 93.

Behr J P et al. Nucleic acid containing composition, preparation and uses of same. U.S. Pat. No. 6,013,240.

Blessing T, J S Remy, J P Behr. J. Am. Chem. Soc. 120:8519-8520, 1998

Boussif O, Lezoualc'h F, Zanta M A, Mergny M D, Scherman D, Demeneix B, Behr J. A Versatile Vector for Gene and Oligonucleotide Transfer into Cells in Culture and in vivo: Polyethylenimine. Proc Natl Acad Sci USA. 1995, 92:7297-7301.

Chimishkyan J Org Chem USSR 1985, 21:1955.

Coll J L, Chollet P, Brambilla E, Desplanques D, Behr J P, Favrot M. In vivo delivery to tumors of DNA complexed with linear polyethylenimine. Hum Gene Ther. 1999, 10(10):1659-1666.

Fernandez, B. M., Reverdito, A. M., Paolucci, G. A., Perillo, I. A. *J. Heterocyclic Chem.,* 1987, 24, 1717.

Ferrari S, Pettenazzo A, Garbati N, Zacchello F, Behr J P, Scarpa M. Polyethylenimine shows properties of interest for cystic fibrosis gene therapy. Biochim Biophys Acta. 1999, 1447(2-3):219-225.

Garcia J, Vilarrasa J. New synthetic "tricks" using old reagents. A mild method for the conversion of RCONHR' to RCONHR". Tett Lett. 1982, 23(10): 1127-1128.

Goula D, Remy J S, Erbacher P, Wasowicz M, Levi G, Abdallah B, Demeneix B A. Size, diffusibility and transfection performance of linear PEI/DNA complexes in the mouse central nervous system. Gene Ther. 1998, 5(5):712-717.

Gruseck U, Heuschmann M, *Chem Ber.* 1987, 120, 2053-2064.

Hafferl W, Lundin R, Ingrahm L L, *Biochemistry,* 1963, 2, 1298.

Jaenicke L, Brode E. *Ann Chem.,* 1959, 624, 120.

Jeong J H, Song S H, Lim D W, Lee H, Park T G. DNA transfection using linear poly(ethylenimine) prepared by controlled acid hydrolysis of poly(2-ethyl-2-oxazoline). J Controlled Release. 2001, 73(2-3):391-399.

Krammer. ACIEE 1977, 16:861.

Krammer. Helv Chim Acta 1978, 61:1342.

Lasic D D, Strey H, Stuart M C A, Podgornik R, Frederik P M. *J Am Chem Soc,* 1997, 119, 832-833.

Leonard B. J Org. Chem. 1965, 30, 817.

Leonard Zwanwenburg. J Am Chem Soc. 1967, 89, 4456.

Lloyd D, McNab H, Marshall D R, *J Chem Soc Perkin Trans. I,* 1978, 1460.

May M, Bardos T J, Barger F L, Lansford M, Ravel J M, Sutherland G L, Shive W. *J Am Chem Soc.* 1951, 73, 3067.

New R C, p. 1, chapter 1, "Introduction" in Liposomes: A Practical Approach, ed. R. C. New IRL Press at Oxford University Press, Oxford, 1990.

Niven R, Pearlman R, Wedeking T, Mackeigan J, Noker P, Simpson-Herren L, Smith J G. *J Pharm Sci.,* 1998, 87, 1292.

Perillo I, Lamdan S. *J Chem Soc Perkin Trans. I,* 1975, 894.

Pfeil, Harder. Angew Chime Int Ed Engl. 1965, 44 518.

Salerno A, Ceriani V, Perillo I A. *J Heterocyclic Chem.* 1992, 29, 1725.

Stach. Tettrahedron 1988, 44:1573-1590.

Stevens M P. Polymer Chemistry: An Introduction New York Oxford University Press 1990.

Strzelecka T E, Rill R L. A 23Na—NMR study of sodium-DNA interactions in concentrated DNA solutions at low-supporting electrolyte concentration. Biopolymers. 1990, 30(7-8):803-814.

Strzelecka T E, Rill R L. Phase transitions of concentrated DNA solutions in low concentrations of 1:1 supporting electrolyte. Biopolymers. 1990, 30(1-2):57-71.

Trubetskoy V S, A Loomis, J E Hagstrom, V G Budker, J A Wolff. Nucleic Acids Res. 27:3090-3095, 1999b.

Trubetskoy V S, A Loomis, P M Slattum, J E Hagstrom, V G Budker, J A Wolff. Bioconjugate Chem. 10:624-628, 1999a.

Trubetskoy V S, P M Slattum, J E Hagstrom, J A Wolff, V G Budker. Anal Biochem. 267:309-313, 1999c.

Trubetskoy V S, V G Budker, L J Hanson, P M Slattum, J A Wolff, L E Hagstrom. Nucleic Acids Res. 26:4178-4185, 1998.

U.S. Pat. No. 08/778,657
U.S. Pat. No. 09/000,692
U.S. Pat. No. 09/070,299
U.S. Pat. No. 09/464,871
U.S. Pat. No. 09/724,089 von Harpe A, Petersen H, Li Y, Kissel T. Characterization of commercially available and synthesized polyethylenimines for gene delivery. J Controlled Release. 2000, 69(2):309-322.

Wilson R W, Bloomfield V A. Counterion-induced condesation of deoxyribonucleic acid. a light-scattering study. Biochemistry. 1979, 18(11):2192-2196.

Wolff J A, Malone R W, Williams P, Chong W, Acsadi G, Jani A, Feigner P L. Direct gene transfer into mouse muscle in vivo. Science, 1990, 1465-1468.

We claim:

1. A process for delivering a polynucleotide to a cell comprising: associating a cationic poly cyclic imidazolinium-containing compound capable of condensing nucleic acid with the polynucleotide to form a complex and contacting the cell with the complex.

2. The process of claim 1 wherein the polynucleotide consists of DNA.

3. The process of claim 1 wherein the polynucleotide consists of RNA.

4. The process of claim 1 wherein the polynucleotide consists of an siRNA.

5. The process of claim 1 wherein the poly cyclic imidazolinium consists of a partially acylated polyethylenimine.

6. The process of claim 5 wherein the partially acylated polyethylenimine consists of an N-propionyl polyethylenimine derivative.

7. The process of claim 5 wherein the polyethylenimine consists of linear polyethylenimine.

8. The process of claim 1 wherein the poly cyclic imidazolinium consists of partially acylated polyallylamine.

9. The process of claim 1 wherein the poly cyclic imidazolinium consists of partially acylated polyvinylamine.

10. The process of claim 1 wherein the cell consists of an in vivo cell.

11. The process of claim 10 wherein the in vivo cell consists of a lung cell.

12. The process of claim 10 wherein the in vivo cell consists of a liver cell.

13. The process of claim 12 wherein the liver cell consists of a hepatocyte.

14. The process of claim 1 further comprising: associating a polyanion with the complex to form a ternary complex having a negative ζ-potential.

* * * * *